(12) United States Patent
Pettersson

(10) Patent No.: US 7,815,940 B2
(45) Date of Patent: *Oct. 19, 2010

(54) GASTRIC ACID SECRETION INHIBITING COMPOSITION

(75) Inventor: Anders Pettersson, Kode (SE)

(73) Assignee: Orexo AB, Uppsala (SE)

( * ) Notice: Subject to any disclaimer, the term of this patent is extended or adjusted under 35 U.S.C. 154(b) by 799 days.

This patent is subject to a terminal disclaimer.

(21) Appl. No.: 10/475,254

(22) PCT Filed: Apr. 17, 2002

(86) PCT No.: PCT/SE02/00757

§ 371 (c)(1),
(2), (4) Date: Dec. 12, 2003

(87) PCT Pub. No.: WO02/083132

PCT Pub. Date: Oct. 24, 2002

(65) Prior Publication Data

US 2004/0131674 A1    Jul. 8, 2004

(30) Foreign Application Priority Data

Apr. 18, 2001    (SE) .................................. 0101379

(51) Int. Cl.
*A61K 9/14* (2006.01)
*A61K 9/16* (2006.01)
*A61K 9/20* (2006.01)
*A61K 9/24* (2006.01)
*A61K 9/48* (2006.01)

(52) U.S. Cl. ...................... 424/489; 424/451; 424/464; 424/472; 424/490

(58) Field of Classification Search ........................ None
See application file for complete search history.

(56) References Cited

U.S. PATENT DOCUMENTS

| | | | |
|---|---|---|---|
| 4,283,408 A | | 8/1981 | Hirata et al. |
| 5,204,118 A | * | 4/1993 | Goldman et al. ............ 424/489 |
| 5,244,670 A | | 9/1993 | Upson et al. ................ 424/439 |
| 5,651,987 A | | 7/1997 | Fuisz |
| 5,840,737 A | | 11/1998 | Phillips ...................... 514/338 |
| 6,013,680 A | * | 1/2000 | Ogawa et al. ............ 424/94.63 |
| 6,077,830 A | * | 6/2000 | Vertesy et al. ................ 514/25 |
| 6,132,768 A | | 10/2000 | Sachs et al. |
| 6,132,771 A | * | 10/2000 | Depui et al. ................ 424/468 |
| 6,183,776 B1 | | 2/2001 | Depui et al. |
| 6,274,173 B1 | | 8/2001 | Sachs et al. |
| 6,316,469 B1 | | 11/2001 | Krishnan et al. |
| 6,489,346 B1 | | 12/2002 | Phillips ...................... 514/338 |
| 6,645,988 B2 | | 11/2003 | Phillips ...................... 514/338 |
| 6,699,885 B2 | | 3/2004 | Phillips ...................... 514/338 |
| 6,852,739 B1 | * | 2/2005 | Garvey et al. ................ 514/338 |
| 6,949,264 B1 | * | 9/2005 | McGrew et al. .................. 426/3 |
| 2004/0171646 A1 | | 9/2004 | Phillips ...................... 514/338 |
| 2005/0054682 A1 | * | 3/2005 | Phillips ...................... 514/338 |

FOREIGN PATENT DOCUMENTS

| | | |
|---|---|---|
| DE | 19925710 | 12/2000 |
| EP | 0005129 | 10/1979 |
| EP | 0166287 | 1/1986 |
| EP | 0 338 861 | 10/1989 |
| GB | 2163747 | 3/1986 |
| GB | 2342292 A * | 4/2000 |
| JP | 2000-63280 | 2/2000 |
| WO | WO90/06925 | 6/1990 |
| WO | WO91/19711 | 12/1991 |
| WO | WO91/19712 | 12/1991 |
| WO | WO 93/11750 A1 | 6/1993 |
| WO | WO94/27988 | 12/1994 |
| WO | WO 95/01780 | 1/1995 |
| WO | WO95/01977 | 1/1995 |
| WO | WO 95/22320 | 8/1995 |
| WO | WO 9522320 A1 * | 8/1995 |
| WO | WO 97/25066 A1 | 7/1997 |
| WO | WO 9725065 A1 * | 7/1997 |
| WO | WO 9725066 A1 * | 7/1997 |
| WO | WO 98/40054 A1 | 9/1998 |
| WO | WO 99/04773 | 2/1999 |
| WO | WO 99/04773 A2 | 2/1999 |
| WO | WO 99/33448 | 7/1999 |
| WO | WO 00/09092 | 2/2000 |
| WO | WO00/78284 | 12/2000 |
| WO | WO2002/083132 | 10/2002 |
| WO | WO 97/25065 | 7/2007 |

OTHER PUBLICATIONS

Peghini et al. "Ranitidine controls nocturnal gastric acid breakthrough on omeprazole: a controlled study in normal subjects"; Gastroenterology 1998, vol. 115:1335-1339.*

Aliment Pharmacol Ther. vol. 13, 1999, M. Geschwantler et al.: "Famotidine versus omeprazole in combination with clarithromycin and metronidazole for eradication of Helicobacter pyroli- a randomized, controlled trial", pp. 1063-1069, abstract, introduction, discussion.

G. Sachs, "Improving on PPI-based therapy of GORD", Europen Journal of Gastroenterology & Hepatology, 13(suppl 1):S35-S41 (2001).

Andersson et al., "Potassium-competitive acid blockade: a new therapeutic strategy in acid-related diseases", Pharmacology & Therapeutics, 108:294-307 (2005).

(Continued)

*Primary Examiner*—S. Tran
(74) *Attorney, Agent, or Firm*—Ryan Kromholz & Manion, S.C.

(57) ABSTRACT

An oral pharmaceutical dosage form comprises pharmacologically effective amounts of an acid susceptible proton pump inhibitor or a salt thereof, an H2 receptor antagonist or a salt thereof and a pharmaceutically acceptable carrier. The dosage form is capable of raising gastric pH to above 4 within two hours after administration and to keep it at that level for at least 4 hours. Also disclosed is a method of manufacture of the dosage form, its use in treating dyspepsia and infection by *Helicobacter pylori*, and a method of treating disorders associated with gastric acid secretion.

12 Claims, 2 Drawing Sheets

OTHER PUBLICATIONS

Cheng, "Combined Use of Proton Pump Inhibitors and Histamine-H2 Receptor Antagonists for GERD: What is the rationale?"*Canadian Phar-maceutical Journal*, Sep. 2002, pp. 27-29,45.

Hirschowitz et al., "Pharmacological Aspects of Acid Secretion" *Digestive Diseases and Sciences*, Feb. 1995; pp. 3S-23S.

Hunt et al, "Optimizing Acid Suppression for Treatment of Acid-Related Diseases"*Digestive Diseases and Sciences*, 1995, vol. 40:24S-49S.

Nwokolo et al., "Tolerance During 29 Days of Conventional Dosing with Cimetidine, Nizatidine, Famotidine or Ranitidin"*Aliment. Pharmacol. Therap.*, 1990, pp. 29-45.

Richardson et al., "Proton Pump Inhibitors, Pharmacology and Rationale for Use in Gastrointestinal Disorders"*Drugs*, Sep. 1998, vol. 56, No. 3, pp. 307-335.

Sachs et al., The Pharmacology of The Gastric Acid Pump: The H+,K+ ATPase,*Annu. Rev. Pharmacol. Toxicol*, 1995; pp. 277-305.

Sachs, George, "Proton Pump Inhibitors and Acid-Related Diseases"*Pharmacotherapy (Reviews of Therapeutics*, 1997; pp. 22-37.

Shin et al., "Structural Aspects of the Gastric H,K ATPase"*Annals New York Academy of Sciences*, 1997; pp. 65-76.

DeGraef et al., "Influence of the Stimulation State of the Parietal Cells on the Inhibitory Effect of Omeprazole on Gastric Acid Secretion in Dogs", *Gastroenterology*, Aug. 1986; vol. 91, No. 2, pp. 333-337.

Hunt, et al., "Optimizing Acid Suppression for Treatment of Acid-Related Diseases"*Digestive Diseases and Sciences*, Feb. 1995; pp. 24S-49S.

Nwokolo et al., "Tolerance During 29 days of Conventional Dosing with Dimetidine, Nizatidine, Famotidine or Ranitidine"*Aliment. Pharmacol. Therap*, 1990, pp. 29-45.

Hirschowitz et al., "Pharmacological Aspects of Acid Secretion"*Digestive Diseases and Sciences*, Feb. 1995; pp. 3S-23S.

Sachs, G., "Proton Pump Inhibitors and Acid-Related Diseases"*Reviews of Therapeutics, (Pharmacotherapy)*, Feb. 1997, pp. 22-37.

Richardson et al., "Proton Pump Inhibitors, Pharmacology and Rationale for Use in Gastrointestinal Disorders"*Drugs*, Sep. 1988, pp. 307-335.

Shin et al., "Structural Aspects of the Gastric H,K ATPase"*Annals of the New York Academy of Sciences* 1997, pp. 65-76.

Sachs et al., "The Pharmacology of the Gastric Acid Pump: The H+K+ ATPase"*Annual Review of Pharmacology and Toxicology*, 1995; pp. 277-305.

Sachs, "Improving on PPI-Based Therapy of GORD",*European Journal of Gastroenterology & Hepatology* , 2001, pp. S35-S41.

Aulton, "Pharaceutics, the Science of Dosage Form Design", , 1988; pp. 289-305.

Huang et al., "pH, Healing and Symptoms in Patients with GERD",*The Yale Journal of Biology and Medicine*, Jun. 1999; pp. 182-194.

Shin et al., "Structural Aspects of the Gastric H,K ATPase"*Annals New York Academy of Sciences*, 1997; pp. 65-76.

Curriculum Vitae (CV) of Nimish Vakil, M.D., FACP, FACG (Exhibit 1 to Vakil Declaration).

Dent, Armstrong, Delany, Moayyedi, Talley, Vakil, "Symptom Evaluation in Reflux Disease: Workshop Background, Processes, Terminology, Recommendations, and Discussion Outputs," Gut 2004; 53 (Suppl IV):iv1-iv24) (Attachment 12 to Vakil Declaration).

Vakil et al, "The Montreal Definition and Classification of Gastroesophageal Reflux Disease: A Global Evidence-Based Consensus," *Am J Gastroenterology* 2006: 101:1900-1920 (Attachment 13 to Vakil Declaration).

Flock, Jones, and Vakil, "Approach to Gastroesophageal Reflux Disease in Primary Care," *Can Fam Physician* 2008; 54:701-5) (Attachment 14 to Vakil Declaration).

American Journal of Gastroenterology, Vol. 96, No. 2, 2001. pp. 303-314, accepted for publication Oct. 6, 2000) (Attachment 2 to Vakil Declaration).

Title 21 U.S.C. § 331.11 (Food and Drugs) (1974) (Attachment 3 to Vakil Declaration).

N. Vakil, "Review Article: Cost-Effectiveness of Different GERD Management Strategies," *Aliment Pharmacol Ther* 2002; 16 (Suppl. 4): 79-82, p. 80) (Attachment 4 to Vakil Declaration).

Vakil, "Novel Methods of Using Proton-Pump Inhibitors," *Gasteroenterol Clin N Am* 31 (2002) S85-88, 87-88) (Attachment 5 to Vakil Declaration).

Vakil et al., "The Effect of Over-the-Counter Rantidine 75 mg on Night-Time Heartburn in Patients With Erosive Oesophagitis on Daily Proton Pump Inhibitor Maintenance Therapy," *Aliment Pharacol Ther* 23 (2006), 649-653) (Attachment 11 to Vakil Declaration).

M. Michael Wolfe, M.D. (Professor, Boston University School of Medicine) and George Sachs, M.D. (Professor, UCLA School of Medicine), "Acid Suppression: Optimizing Therapy for Gastroduodenal Ulcer Healing, Gastroesophageal Reflux Disease, and Stress-Related Erosive Syndrome," *Gastroenterology* 2000; 118:S9-S31 (Attachment 6 to Vakil Declaration).

$6^{th}$ Edition of Schlesinger and Fordtran's *Gastrointestinal and Liver Disease (Pathophysiology/Diagnosis/Management)* (1998) (Attachment 7 to Vakil Declaration).

$5^{th}$ Edition of Schlesinger and Fordtran's *Gastrointestinal and Liver Disease (Pathophysiology/Diagnosis/Management)* (1993) (on pp. 626-627) (Attachment 8 to Vakil Declaration).

United States Patent 5,229,137 (issued Jul. 20, 1993) (Attachment 9 to Vakil Declaration.

Fändriks, Lönroth, Pettersson, *Scandinavian Journal of Gasteroenterology (Scandinavian Journal of Gasteroenterology*, "Can Famotidine and Omeprazole be Combined on a Once-Daily Basis?" 2007; 42: 689-694) (Attachment 10 to Vakil Declaration.

Office Action, Related Application 10/531,598, Mailed Jun. 29, 2007.

Office Action, Related Application 10/531,598, Mailed Feb. 8, 2008.

Office Action, Related Application 10/531,598, Mailed Apr. 30, 2008.

Interview Summary, Related U.S. Appl. No. 10/531,598, May 27, 2009.

Interview Summary, Related U.S. Appl. No. 10/531,598, Mailed Jun. 9, 2009.

Office Action, Related U.S. Appl. No. 10/531,598, Mailed Jul. 1, 2009.

Office Action, Related U.S. Appl. No. 11/544,750, Mailed Jun. 29, 2007.

Office Action, Related U.S. Appl. No. 11/544,750, Mailed Feb. 7, 2008.

Office Action, Related U.S. Appl. No. 11/544,750, Mailed Apr. 29, 2008.

Interview Summary, Related U.S. Appl. No. 11/544,750, May 29, 2009.

Interview Summary, Related U.S. Appl. No. 11/544,750, Mailed Jun. 9, 2009.

Office Action, Related U.S. Appl. No. 11/544,750, Mailed Jun. 26, 2009.

Vakil, American Journal of Gastroenterology, vol. 96, No. 2, 2001. pp. 309) (Attachment 2 to Supplementing Declaration).

M. Schubert et al., "Control of Gastric Acid Secretion in Health and Disease," Gastroenterology 2008; 134: 1842-1860, p. 1842) (Attachment 3 to Supplementing Declaration).

Malagelda et al, "Antacid Therapy," Scand J. Gastroenterol Suppl: 1979; 55: 67-83, p. 72) (Attachment 4 to Supplementing Declaration).

Deering et al, "Comparison of an H2 Receptor Antagonist and a Neutralizing Antacid on Postprandial Acid Delivery Into the Duodenum in Patients with Duodenal Ulcer," Gastroenterology 73: 11-14, 1977, pp. 11 and 13) (Attachment 5 to Supplementing Declaration).

Title 21 U.S.C. § 331.11 (Food and Drugs) (1974) (Attachment 6 to Supplementing Declaration).

Cramer, "What's an Antacid?", FDA Consumer, Jan.-Feb., 1992, Attachment 7 to Supplementing Declaration).

Richter, "Review Article: The Management of Heartburn in Pregnancy," Aliment Pharmacol Ther 2005: 22: 749-757, p. 751) (Attachment 8 to Supplementing Declaration).

McGrew et al United States Patent 6,949,264 (Attachment 9 to Supplementing Declaration).

Vertesy et al. United States Patent 6,077,830 (Attachment 10 to Supplementing Declaration).

Zyck et al U.S. Appl. No. 2001/0,021,403 (Attachment 11 to Supplementing Declaration).

"The Next Blockbuster Drugs" (Newsweek, Jul. 22, 2009) (Attachment 12 to Supplementing Declaration).

Eriksson, E. et al., "Omeprazole and $H_2$-receptor antagonists in the acute treatment of duodenal ulcer, gastric ulcer and reflux oesophagitis: a meta-analysis", *European Journal of Gastroenterology & Hepatology*, 7:467-475 (1995).

Hedenström, H. et al., "Intragastric pH after oral administration of single doses of ranitidine effervescent tablets, omeprazole capsules and famotidine fast-dissolving tablets to fasting healthy volunteers", *Aliment Pharmacol Ther*, 11:1137-1141 (1997).

Hurlimann S. et al., "Comparison of acid inhibition by either oral high-dose ranitidine or omeprazole", *Aliment Pharmacol Ther*, 8:193-201 (1994).

Hunyady B. et al., "Statistical interpretation of the antisecretory effect of famotidine measured by intragastric pH-metry", *Eur J Clin Pharmacol*, 50:449-456 (1996).

Peghini, P. et al., "Ranitidine Controls Nocturnal Gastric Acid Breakthrough on Omeprazole: A Controlled Study in Normal Subjects", *Gastroenterology*, 115:1335-1339 (1998).

Katz, P. et al., "Histamine receptor antagonists, proton pump inhibitors and their combination in the treatment of gastro-oesophageal reflux disease", *Best Practice & Research Clinical Gastroenterology*, 15(3):371-384 (2001).

Andersson, T. et al., "Influence of acid secretory status on absorption of omeprazole from enteric coated granules", *Br. J. clin. Pharmac.*, 31:275-278 (1991).

\* cited by examiner

GASTRIC ACID SECRETION INHIBITING COMPOSITION

CROSS REFERENCE TO RELATED APPLICATION

The present application is a 35 U.S.C. §371 national phase conversion of PCT/SE02/00757, filed Apr. 17, 2002, which claims priority of Swedish Application No. 0101379-6 filed Apr. 18, 2001.

FIELD OF THE INVENTION

The present invention relates to a gastric acid secretion inhibiting composition, to a method for its manufacture and to its use in treating conditions which are related to the secretion of gastric acid.

BACKGROUND OF THE INVENTION

Dyspepsia (acid dyspepsia) is a common disorder. Heartburn is a symptom of dyspepsia. It is estimated that 44% of Americans have heartburn at least once monthly but that only about 25% of them are seeing the doctor because of their dyspepsia problem. Symptoms associated with dyspepsia are for instance upper abdominal pain/discomfort and heartburn, indigestion, "sour" stomach, and gastro-esophageal reflux.

Dyspepsia is a multi-factorial disease and may be associated with organic pathology such as duodenal ulcer, gastric ulcer, esophagitis, Barrett's esophagus or gastro-duodenal inflammation (e.g., *Helicobacter pylori* infection). Dyspepsia also includes conditions where no organic pathology can be found, e.g., non-ulcer dyspepsia (NUD) or functional dyspepsia.

Dyspepsia can be controlled by administration of medicines that reduce the pH in the stomach. Therapeutic agents effective in the treatment of dyspepsia include gastric acid suppressing agents, such as histamine H2 receptor antagonists (in the following called H2 receptor antagonists), acid susceptible proton pump inhibitors, antacids/alginates, anticholinergics and prokinetic agents. They can be distinguished by their mechanism of action, safety profile, and pharmacokinetics. The stomach pathogen *Helicobacter pylori* has been associated with dyspepsia, gastro-duodenal ulcer disease and stomach cancer. The treatment of *H. pylori* infection usually comprises the administration of a combination of acid secretion suppressing agents and one or two antibiotic agents.

The therapeutic effect on dyspepsia related discomfort and organic lesions when inhibiting acid production by administration of acid secretion-inhibiting drugs is related to the degree of acid inhibition as well as to the onset and duration of action of the particular drug. The majority of patients who have symptomatic acid reflux disease have a normal esophageal mucosa or only a mild degree of esophagitis. Treatment to relieve symptoms as they occur may be the best way to manage these patients, to whom the speed of symptom relief is of primary importance.

Antacid agents, that is, acid neutralizing agents, and alginates are the first therapeutic choice in the treatment of mild heartburn. They have a extremely short duration of action but are seen as inexpensive and safe. Antacid agents work locally through a neutralization of gastric acid. Alginates provide some mechanical protection against reflux of gastric acid into the esophagus. The main advantages of antacid agents and alginates are, that they provide fast relief of symptoms. The main disadvantage of antacid agents and alginates is the extremely short duration of action and dosing has to be repeated frequently to keep the patients free of symptoms, further that antacids often do not provide symptom resolution, i.e. complete relief of symptoms.

Several classes of compounds are known which affect the secretion of gastric acid. Among them proton pump inhibitors, such as the substituted benzimidazoles omeprazole, lansoprazole, rabeprazole, pantoprazole, and H2 receptor antagonists, such as cimetidine, ranitidine, famotidine, are the most prominent ones. H2 receptor antagonists and acid susceptible proton pump inhibitors are widely prescribed for reducing gastric acid secretion systemically. After 5 days' treatment, acid susceptible proton pump inhibitors have in clinical studies been proven to be very effective in providing symptom resolution in patients with dyspepsia associated with gastric ulcers, duodenal ulcers, reflux esophagitis and gastro-esophageal reflux without esophagitis. Acid susceptible proton pump inhibitors and H2 receptor antagonists, respectively, have also proven to be effective in curing *H. pylori* infection in combination with one or two antibiotics (Gschwandtler M et al., *Aliment Pharmacol Ther* 1999, 13(8):1063-9). It is established that omeprazole is superior to H2 receptor antagonists regarding healing of gastro-duodenal and esophageal lesions as well as providing dyspeptic symptom resolution in these conditions (Eriksson S., *European Journal of Gastroenterology & Hepatology* 1995, 7:465).

Various combinations of antacid and/or mucosa protecting agents with agents that reduce acid secretion have been disclosed to be useful in treating dyspepsia.

WO 95/017080 describes a composition for use in the treatment of for instance heartburn comprising an H2 receptor antagonist, such as famotidine, and an alginate and optionally simethicone (an activated polysiloxane).

EP 338861 A describes a solid pharmaceutical preparation consisting of an antacid and excipients which is proposed to be used in combination with an acid susceptible proton pump inhibitor or any other substance inhibiting gastric acid secretion. There is no suggestion to combine these substances in a fixed unit dosage form.

U.S. Pat. No. 5,244,670 A describes an ingestible pharmaceutical composition comprising a substance selected from the group consisting of antacid agents, acid secretion prevention agents, bismuth-containing agents and their mixtures, and 3-(1-menthoxy)-propane-1,2-diol which is present to provide a cooling sensation to the throat.

WO 97/25066 discloses a pharmaceutical formulation comprising a combination of an acid susceptible proton pump inhibitor or an H2 receptor antagonist and one or more antacid agents or alginates.

Neither acid susceptible proton pump inhibitors nor H2 receptor antagonists, alone or in combination with antacids and/or alginates, provide fully satisfactory quick and lasting relief to patients, to whom the speed of symptom relief is of primary importance but who also desire to be free of symptoms for a longer period of time.

OBJECTS OF THE INVENTION

It is an object of the invention to provide a medicine which provides quick and lasting relief to a patient suffering from conditions related to gastric acid secretion.

It is another object of the invention to provide a method for treating a patient suffering from conditions related to gastric acid secretion which provides quick and lasting relief.

Further objects of the invention will be evident from the following short description of the invention, a preferred embodiment thereof, and the appended claims.

SUMMARY OF THE INVENTION

The present invention is based on the insight that acid susceptible proton pump inhibitors and H2 receptor antagonists possess mutually supplementing properties in respect of inhibiting acid secretion and that they can be used for designing a pharmaceutical composition which provides quick and lasting relief to a patient suffering from conditions related to gastric acid secretion.

Acid susceptible proton pump inhibitors are acid activated prodrugs that covalently inhibit the gastric H+,K+-ATPase, the proton-transporting enzyme involved in the production of hydrochloric acid in the stomach. The action of gastric H+,K+-ATPase represents the final step in the sequence of events resulting in secretion of hydrochloric acid by the parietal cell. Thus inhibition of this enzyme is the most effective and specific means of controlling acid secretion regardless of the nature of the stimulus to secretion. As would be expected with such a mechanism of action, omeprazole has been shown to inhibit both basal and stimulated acid secretion. Omeprazole is a weak base which accumulates in the acidic milieu of the secretory membrane of the parietal cell where it undergoes rearrangement in acid to its active sulphenamide form which subsequently reacts with sulfhydryl groups of the acid pump.

In gastric mucosa, the acid susceptible proton pump is situated in the apical membrane and in the tubovesicles bordering the secretory canaliculi of the parietal cell. Thus, after a single dose, omeprazole rapidly accumulates in the acidic compartment of the secretory membrane where its active sulphenamide form irreversible binds to the H+,K+-ATPase. The H+,K+-ATPase situated in the tubovesicles will however not be exposed for activated omeprazole. A major portion of synthesized H+,K+-ATPase will thus escape blockade after a single omeprazole dose. This may explain why the maximal acid inhibitory effect of omeprazole is reached only after about five days treatment.

H2 receptor antagonists competitively inhibit the action of histamine on all H2 receptors, mainly on the surface of the parietal cells. At therapeutic doses these agents are capable not only of decreasing both basal and nocturnal acid secretion, but also secretion stimulated by food, histamine, insulin and pentagastrin. A single dose of an H2 receptor antagonist results in maximal acid inhibitory effect already within 2 hours after intake. Furthermore, the acid inhibitory effect obtained with high doses of an H2 receptor antagonist is built up rapidly but has a tendency to fade substantially during the following 2-7 days, while the acid inhibitory effect of omeprazole gradually is built up during the same period of time.

According to the invention, by combining an H2-receptor antagonist with an acid susceptible proton pump inhibitor, it is possible to obtain rapid onset of action as well as good long-term efficacy.

Thus, according to the invention, is provided an oral pharmaceutical dosage form comprising pharmacologically effective amounts of an acid susceptible proton pump inhibitor or a salt thereof, and an H2 receptor antagonist or a salt thereof, and a pharmaceutically acceptable carrier. The terms "proton pump inhibitor" and "H2 receptor antagonist" include their isomers, such as enantiomers of proton pump inhibitors, as well as pharmaceutically acceptable salts of such isomers.

The invention is especially suitable for "on demand" treatment of gastro-esophageal reflux complaints e.g. heartburn, where potent acid reduction is needed for a shorter period of time and where a rapid onset of action is most important and a maximal acid reduction is to prefer. The maximal acid inhibitory effect would be able to be maintained during a 7 days period by the elimination of the "fade-off" phenomenon seen after H2-blocker given alone. This will be important in order to reduce the time for the treatment of stomach ulcers, acid related lesions in the esophagus and *Helicobacter pylori* eradication.

According to the invention is provided an oral dosage form comprising an H2 receptor antagonist in an amount effective to reduce the acidity in the stomach after administration and an acid susceptible proton pump inhibitor in an amount effective to sustain the low acidity effected by the H2 receptor antagonist over an extended period of time. It is preferred for the pharmacologically effective amounts to be amounts capable of raising gastric pH to above 3 within 2 hours from administration and to keep it above 3 for at least 4 hours, preferably for at least 8 hours. It is more preferred for said pharmacologically effective amounts to be amounts capable of raising gastric pH to above 4 within two hours after administration and to keep it above 4 for at least 4 hours, more preferred for at least 8 hours.

According to a first preferred aspect of the invention the H2 receptor antagonist is provided in an amount which is capable of providing at least 80% of maximal reduction, more preferred at least 95% of maximal reduction, of the acidity in the stomach within about two hours. "Maximal reduction" is the reduction of acidity which can be maximally obtained by administering an H2 receptor antagonist alone in therapeutically accepted amounts, that is, in amounts in which such drugs are administered in the art. The term "H2 receptor antagonist(s)" as used herein includes all agents that substantially inhibit or block the secretion of gastric acid by binding to a histamine receptor in the stomach. At therapeutic doses such H2 receptor antagonists are capable not only of decreasing basal and nocturnal acid secretion, but also secretion stimulated by food, histamine, insulin and pentagastrin. Exemplary H2 receptor antagonists according to the invention are cimetidine, ranitidine, nizatidine and famotidine which are normally used in form of their pharmacologically acceptable salts, in particular hydrochlorides. The dosage form of the invention preferably comprises from 1 mg to 800 mg of H2 receptor antagonist or salt thereof, more preferred from 5 mg to 400 mg.

According to a second preferred aspect of the invention the acid susceptible proton inhibitor is provided in an amount which is capable of maintaining the low acidity effected by the histamine H2 antagonist over at least 6 hours. Acid susceptible proton pump inhibitors are rapidly taking market share from H2 receptor antagonists. The term "acid susceptible proton pump inhibitor(s)", as used herein, comprises benzimidazole derivatives having substantial H+,K+-ATPase inhibiting activity, in particular omeprazole, pantoprazole, lanzoprazole, rabeprazole, pariprazole, leminoprazole and their pharmaceutically acceptable salts and enantiomers and salts of enantiomers, but include also the other compounds disclosed on pages 7-11 of WO 97/25066 which are hereby incorporated by reference as well as those disclosed in EP 005 129 A1, EP 174 726 A1, EP 166 287 A1, GB 2 163 747, WO 90/06925, WO91/19711, WO91/19712, WO94/27988, WO95/01977. Omeprazole is known to offer significant gain over H2 receptor antagonists in terms of symptom resolution, healing and prevention of relapse. 3.

Thus the dosage form of the invention comprises preferably from 1 mg to 100 mg, more preferred from 5 mg to 50 mg, per single dose of an acid susceptible proton pump inhibitor or a salt thereof. Preferably the acid susceptible proton pump inhibitor or salt thereof is separated from the H2 receptor antagonist by an enteric coating.

According to a fourth preferred aspect of the invention the H2 receptor antagonist and the acid susceptible proton pump inhibitor need not to be comprised by the same pharmaceutical composition but may be administered separately but within a narrow time interval, such as a time interval of one hour, in particular a time interval of 30 min, most preferred a time interval of 10 min. Thus is disclosed a corresponding dose regimen for separate but joint administration of an acid susceptible proton pump inhibitor and an H2 receptor antagonist to treat a condition related to gastric acid secretion.

The oral dosage form of the invention thus comprises an acid susceptible proton pump inhibitor, an H2 receptor antagonist and a pharmaceutical carrier and, optionally, a gastric acid suppressing agent and/or an alginate. Preferably, the dosage form of the invention comprises from 100 mg to 1000 mg of antacid agent and/or alginate. The antacid agent of the invention comprises one or several of aluminum hydroxide, calcium carbonate, magnesium carbonate, basic magnesium carbonate, magnesium hydroxide, magnesium oxide, sodium hydrogen carbonate.

According to a fifth preferred aspect of the invention the bioavailability of the acid susceptible proton pump inhibitor is improved for the first three consecutive doses of a dose regimen or composition of the invention in the treatment of dyspepsia, in particular the first five consecutive doses, since less proton pump inhibitor will be degraded during passage of the drug through the stomach.

Due to the fact that acid susceptible proton pump inhibitors are generally sensitive to acid (acid susceptible proton pump inhibitors) they need to be administered in a form which protects them from degradation in the stomach to make them pass into the small intestine where they are absorbed. H2 receptor antagonists, on the other hand, can be administered without such protection. According to a further preferred aspect of the invention, compositions can be adapted to suit the purpose of the present invention are among those disclosed in WO 97/25066.

The oral dosage forms of WO 97/25066 comprise an acid susceptible proton pump inhibitor in an amount similar or identical to that used in the composition of the present invention, and one or several antacid agents and/or alginate(s). The adaptation of the compositions of WO 97/25066 essentially consists in substituting a pharmacologically effective amount of an H2 receptor antagonist for a portion of or the entire amount of the antacid agent(s) and/or alginate.

According to the invention is provided an oral, multiple unit tableted dosage form comprising an acid susceptible proton pump inhibitor in individually enteric coating layered units in combination with an H2 receptor antagonist in the form of a powder or granules compressed into a tablet. The enteric coating layer(s) covering the individual units of the acid susceptible proton pump inhibitor has properties such that the compression of the units into a tablet does not significantly affect the acid resistance of the individually enteric coating layered units. Furthermore, the multiple unit tableted dosage form provides a good stability to the active substances during long-term storage.

According to the invention is also provided a multiple unit tableted dosage form, which is divisible and easy to handle. Such a multiple unit tableted dosage form comprises enteric coating layered pellets of an acid susceptible proton pump inhibitor compacted with a pulverous H2-antagonist. This dosage form may also contain effervescent components for making it rapidly disintegrate when put into water; the pH of the aqueous phase thereby must be made slightly acidic to prevent dissolution of the enteric layer. This dosage for can be given to patients with swallowing disorders and in pediatrics. Such a suspension of dispersed units/pellets of appropriate size can be used for oral administration and also for feeding through a naso-gastric tube.

According to the invention is also provided a tablet preparation comprising an acid susceptible proton pump inhibitor in admixture with tablet excipients forming a tablet core which is enterically coated, and a separate layer surrounding the tablet core. The surrounding layer comprises an H2 receptor antagonist in admixture with a pharmaceutical carrier. Optionally a separating layer is applied on the tablet core before the core is enteric coating layered. Alternatively, the prepared tablet is sectioned in separate layers, each one comprising different active substances. One of the layers, preferably the innermost layer (core), comprises the acid susceptible proton pump inhibitor in the form of enteric coating layered pellets in admixture with pharmaceutical excipients and the other layer(s) comprise(s) the histamine H2-antagonist(s), respectively in admixture with pharmaceutical excipient(s). Optionally the two layers are separated by a separating layer to prevent tacking between the two layers. The core comprising the acid susceptible proton pump inhibitor may also be advantageously coated directly with an enteric layer by following, for instance, procedures disclosed in WO 00/78284 which is incorporated herein by reference.

According to the invention the acid susceptible proton pump inhibitor in the form of enteric coating layered pellets may be mixed with histamine H2-antagonist(s) and optionally pharmaceutical excipient(s) to be administered in a sachet intended for oral administration after dispersion in a slightly acidic aqueous solution.

It is thus preferred for the dosage form of the invention to comprise the acid susceptible proton pump inhibitor or a salt thereof protected by an enteric coating layer and, optionally, a layer separating it from the enteric coating. Preferably the dosage form of the invention comprises two concentric layers optionally separated by one or more separating layer(s), one layer comprising said acid susceptible proton pump inhibitor or salt thereof, the other layer comprising said H2 receptor antagonist or salt thereof. The inner layer comprises the acid susceptible proton pump inhibitor or salt thereof and the outer layer comprises the H2 receptor antagonist or salt thereof. According to the invention it is also possible for the outer layer to comprise the acid susceptible proton pump inhibitor or salt thereof and fort the inner layer to comprise the H2 receptor antagonist or salt thereof. According to a preferred aspect the inner layer comprises a disintegrant. The oral dosage form of the invention may take different shapes, such as a tablet, a capsule, a divided powder/pellet formulation, and the like.

According to the invention is also disclosed a method for the manufacture of an oral tableted dosage form comprising amounts of an acid susceptible proton pump inhibitor or salt thereof and an H2 receptor antagonist or salt thereof pharmacologically effective in treating a condition related to dyspepsia, the method comprising forming a first layer comprising said acid susceptible proton pump inhibitor or salt thereof, an enteric coat surrounding said first layer, and a second layer comprising said H2 receptor antagonist or salt thereof surrounding said first layer and said enteric coat. Also disclosed is a method for the manufacture of an oral dosage form comprising amounts of an acid susceptible proton pump inhibitor or salt thereof and an H2 receptor antagonist or salt thereof pharmacologically effective in treating a condition related to dyspepsia, the method comprising forming pellets comprising said acid susceptible proton pump inhibitor or salt thereof, covering said pellets with enteric coat, and mixing said pellets covered with said enteric coat with a carrier comprising said H2 receptor antagonist or salt thereof; the carrier may comprise a disintegrant. The aforementioned methods of the invention further comprise a final tablet forming step, possibly followed by a film-covering step.

Another method for the manufacture of the oral dosage form of the invention comprises filling a capsule capable of disintegrating in gastrointestinal fluids to release its contents with the mixture comprising enteric proton pump inhibitor pellets and a H2 receptor antagonist in powderous or granular form.

A further method for the manufacture of the oral dosage form of the invention comprises forming a layer comprising an acid susceptible proton pump inhibitor or salt thereof and an H2 receptor antagonist or salt thereof, and covering said layer with an enteric coat.

A still further method for the manufacture of the oral dosage form of the invention comprises forming a mixture comprising an acid susceptible proton pump inhibitor or salt thereof and an H2 receptor antagonist or salt thereof, filling the mixture in a capsule capable of disintegrating in gastrointestinal fluids to release its contents, and covering the capsule with an enteric coat.

The use of the pharmaceutical dosage form of the invention is however not restricted to provide quick and lasting relief to a patient suffering from conditions related to gastric acid secretion. The rapid onset of inhibition of gastric acid secretion combined with the maintenance of inhibition as long as desired (by repeated administration of a composition comprising an acid susceptible proton pump inhibitor, preferably by repeated administration of the composition of the invention) can be expected to have a positive effect on the healing of esophagitis for which the maintenance of intra-gastric pH above 4 for a maximal duration is acknowledged (Huang J Q and Hunt R H, pH, healing rate and symptom relief in patients with GERD, *Yale J Biol Med* 1999, 72:181-94). The composition of the invention thus is also preferred for maintaining gastric pH above 4 for extended periods of time, such as 4 hours and more.

According to the invention the aforementioned mixture comprising an acid susceptible proton pump inhibitor or salt thereof and an H2 receptor antagonist or salt thereof can be used for the manufacture of a medicament for the treatment of a disorder associated with gastric acid secretion.

The dosage form of the invention can also be used, in association with one or more antibiotic agent(s), for the eradication of *Helicobacter pylori*.

According to the invention is also disclosed a method of treating disorders associated with gastric acid secretion, the method comprising the administration of the dosage form of the invention or the concomitant administration of two separate oral dosage forms, one comprising a pharmacologically effective amount of an acid susceptible proton pump inhibitor or salt thereof, the other comprising a pharmacologically effective amount of an H2 receptor antagonist or salt thereof.

Furthermore, according to the invention is disclosed a method of treating an infection by *Helicobacter pylori*, comprising the administration of the dosage form of the invention or the concomitant administration of two separate oral dosage forms, one comprising a pharmacologically effective amount of an acid susceptible proton inhibitor or salt thereof, the other comprising a pharmacologically effective amount of an H2 receptor antagonist or salt thereof, in association with the administration of one or more antibiotic agent(s) effective against *H. pylori*.

It is preferred for the aforementioned methods of treatment according to the invention to comprise a dose regimen capable of maintaining gastric pH above 4 for at least 95% of the time period starting at 2 hours from the administration of the first dose and extending until 6 hours from the administration of the last dose, in particular a regiment wherein the time period is one week or more, preferably two weeks or more, even more preferred four weeks or more. Also preferred in this context is a dose regimen capable of maintaining gastric pH above 3 for at least 95% of the time period starting at 2 hours from the administration of the first dose and extending until 6 hours from the administration of the last dose, in particular for four weeks or more.

The invention will now be described in greater detail by reference to a number of preferred but not limiting embodiments illustrated in a drawing.

BRIEF DESCRIPTION OF THE FIGURES

FIG. 1 a multiple unit tableted dosage form comprising an acid susceptible proton pump inhibitor in the form of enteric coating layered pellets in admixture with an H2-receptor antagonist dispersed in a pharmaceutical carrier;

FIG. 2 a tableted dosage form consisting of two halves, one of which comprises enteric coating layered pellets of an acid susceptible proton pump inhibitor in admixture with excipients whereas the other comprises an H2 receptor antagonist in admixture with excipients;

FIG. 3 a multiple-layered tableted dosage form comprising an acid susceptible proton pump inhibitor in a core surrounded by an enteric coating layer and a layer containing an H2 receptor antagonist dispersed in a pharmaceutical carrier surrounding the core;

FIG. 4 a tableted dosage form comprising an acid susceptible proton pump inhibitor, an H2-receptor antagonist and excipients in admixture, provided with an enteric coating;

FIG. 5 a capsule dosage form containing an acid susceptible proton pump inhibitor in enteric coating layered pellets in admixture with an H2 receptor antagonist and pharmaceutical excipients;

FIG. 6 an acid resistant capsule dosage form containing an acid susceptible proton pump inhibitor, an H2 receptor antagonist and excipients;

DESCRIPTION OF PREFERRED EMBODIMENTS

Figure 1:
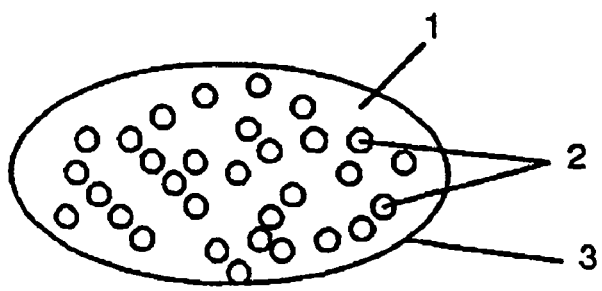
FIGS. 1-6 are schematic cross sections illustrating.

Multiple unit tableted dosage form. The multiple unit tableted dosage form of the invention illustrated in FIG. 1 consists of a tablet body 1 optionally covered by a film layer 3 and small pellets 2 distributed at random in the tablet body 2. The pellets 2 contain an acid susceptible proton pump inhibitor in form of the racemate, an alkaline salt or one of its enantiomers. The individually enteric coating layered units 2 (small beads, granules or pellets) containing the acid susceptible proton pump inhibitor and optionally containing alkaline substances, are mixed with the H2 receptor antagonist and conventional tablet excipients forming, in combination, the tablet body 1. The H2 receptor antagonist and tablet excipients may be dry mixed or wet mixed into granules. The mixture of enteric coated layered units, H2 receptor antagonist and excipients are compressed into the multiple unit tableted dosage forms. By the expression "individual units" is meant small beads, granules or pellets, in the following referred to as proton pump inhibitor pellets. In compressing the mixture into tablets, care must be taken not to significantly affect the acid resistance of the enteric coated layered pellets. In regard of the core material for enteric coating layered pellets comprising an acid susceptible proton pump inhibitor reference is made to WO 97/25066, page 13, next but last paragraph, to page 15, end of second paragraph, which are hereby incorporated by reference. In regard of the enteric coating layer(s) reference is made to WO 97/25066, page 15, next but last paragraph, to page 18, end of second paragraph, which are hereby incorporated by reference. The acid susceptible proton pump inhibitor pellets covered with enteric coating layer(s) may be further covered with one or more overcoating layers. In regard of such over-coating layer(s) reference is made to WO 97/25066, page 18, last paragraph, to page 19, end of first paragraph, which are hereby incorporated by reference. The H2 receptor antagonist is dry mixed with inactive excipients such as filler, binders, disintegrants, and other pharmaceutically acceptable additives. The mixture is wet massed with a granulation liquid. The wet mass is dried preferably to a loss on drying of less than 3% by weight. Then the dry mass is milled to a suitable size for granules, preferably smaller than 1 mm. Suitable inactive excipients are, for instance, mannitol, corn starch, potato starch, low substituted hydroxypropyl cellulose, microcrystalline cellulose and crosslinked polyvinylpyrrolidone. The dry mixture comprising the H2 receptor antagonist may be mixed with a suitable granulation liquid comprising, for instance, hydroxypropylcellulose or polyvinylpyrrolidone dissolved in water or alcohol or their mixtures. Alternatively the H2 receptor antagonist is dry mixed with pharmaceutically acceptable excipients (see supra).

Multi unit tablets. The enteric coated layered pellets comprising an acid susceptible proton pump inhibitor are mixed with the H2 receptor antagonist granules or with the prepared dry mixture comprising the H2 receptor antagonist. The mixture is admixed with lubricant(s) and compressed into a multiple unit tableted dosage form. Suitable lubricants for the tableting process are, for instance, sodium stearyl fumarate, magnesium stearate and talc. The compressed tablets are optionally covered with filmforming agent(s) to obtain a smooth surface. Such coating layer may further comprise additives such as anti-tacking agents, colorants and pigments or other additives.

The fraction of enteric coating layered pellets constitutes preferably less than 60% by weight of the total tablet weight. The preferred multiple unit table formulation thus consists of enteric coated layered pellets comprising the acid susceptible proton pump inhibitor, optionally in admixture with alkaline reacting compound(s), compressed into tablets with the prepared H2 receptor antagonist/excipient(s) mixture. The enteric coating layer(s) make(s) the pellets of the dosage form insoluble in acidic media but disintegrating/dissolving in near neutral to alkaline media such as, for instance, the gastric fluid present in the proximal part of the small intestine where the dissolution and uptake of the acid susceptible proton pump inhibitor is desired. The enteric coating layered proton pump inhibitor pellets may also be covered with an overcoating layer before being formulated into tablets, and they may also contain one or more separating layer(s) in between the core material and the enteric coating layer(s).

Process for making multi-unit tablets. The process for the manufacture of the dosage form represents a further aspect of the invention. After formulating the pellets by dry mixing (ordered mixture), spray coating or layering of the acid susceptible proton pump inhibitor onto seeds, or by extrusion/ spheronization or granulation, the pellets are first optionally covered with the separating layer(s) and then with the enteric coating layer(s), or a separating layer is spontaneously developed in situ between the core material and the enteric coating layer material. The coating is carried out as described above and in the accompanying examples. The preparation of the H2 receptor antagonist mixture is also described in the examples.

Figure 2:
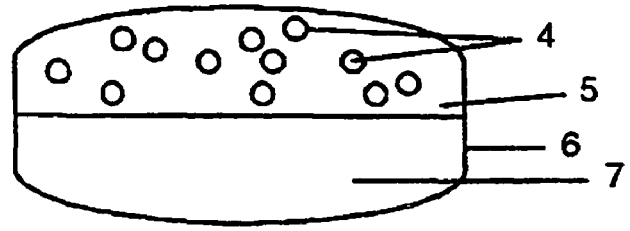
Figure 3:
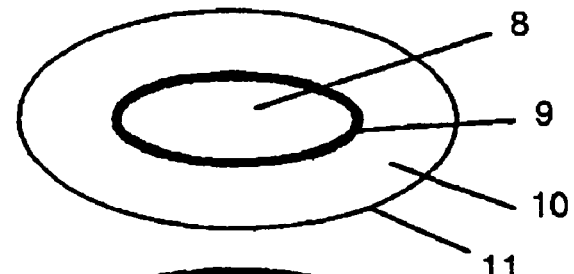

The enteric coating layered pellets, with or without an overcoat, are mixed with the prepared H2 receptor antagonist granules or dry powder, tablet excipients and other pharmaceutically acceptable additives and compressed into tablets. Alternatively, the enteric coated proton pump inhibitor pellets may be covered by a second layer containing the H2 receptor antagonist as described in the following examples. Furthermore, as illustrated in FIG. 2, the enteric coating layered pellets 4 may be intimately mixed with excipients 5 and precompressed and further layered with the H2 receptor antagonist preparation 7 and finally compressed into a tablet, optionally with film-forming agent(s) 6 to obtain a smooth surface. As a further alternative illustrated in FIG. 3 the acid susceptible proton pump inhibitor in form of a powder may be mixed with tablet excipients and compressed into a tablet 8 which is optionally layered with a separating layer and thereafter enteric coating 9 layered. The thus produced tablet core is presscoated with the H2 receptor antagonist preparation 10. Finally the table may be covered with a tablet coat 11 to obtain a smooth surface.

It is also possible to fill the acid susceptible proton pump inhibitor in form of enteric coated layered pellets in a sachet together with H2 receptor antagonist optionally mixed with excipients.

Figure 4:
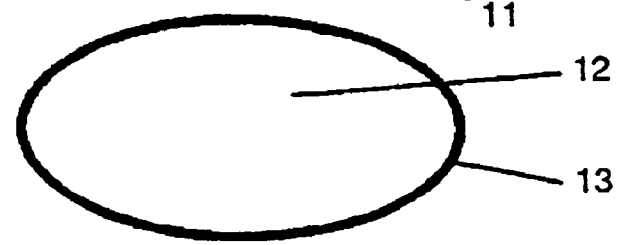

FIG. 4 illustrated a tableted dosage form with a core 12 comprising an acid susceptible proton pump inhibitor and an H2 receptor antagonist dispersed in a pharmaceutical carrier, the core 12 being surrounded by an enteric coat 13.

Figure 5:
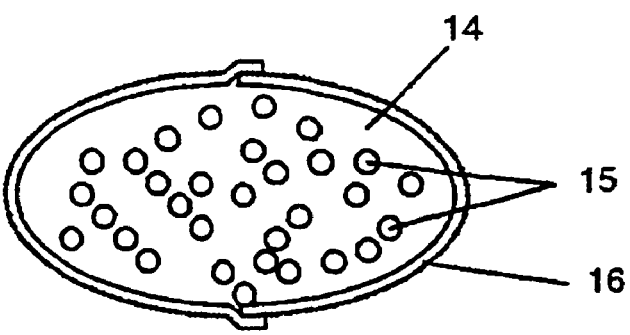

FIG. 5 illustrates a hard gelatin capsule 16 filled with the uncompressed core material 14, 15 of the embodiment of FIG. 1.

Figure 6:
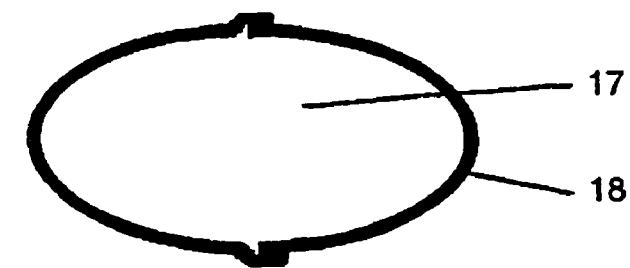

FIG. 6 illustrates a hard gelatin capsule 18 comprising an enteric coat filled with the uncompressed core material 17 of the embodiment of FIG. 4.

In general, the methods of WO 97/25066 for making oral pharmaceutical dosage forms comprising an acid susceptible proton pump inhibitor and an antacid agent or alginate can be adapted to suit the purpose of the invention by substituting part or the entire amount of antacid agent or alginate by a pharmacologically effective amount of an H2 receptor antagonist, the remainder of the antacid agent or alginate (if substitution is not 1:1 by weight) being omitted or substituted by excipients like microcrystalline cellulose, silica, lactose, mannitol, ant the like.

Use of the Dosage Forms According to the Invention.

The dosage forms according to the invention are especially advantageous in the treatment of dyspepsia and other gastrointestinal disorders related to the production of gastric acid to provide quick and lasting relief from symptoms. The dosage forms are administered once or several times a day. The typical daily dose of the acid susceptible proton pump inhibitor and the H2 receptor antagonist will depend on various factors such as individual requirements of patients, the mode of administration, and the particular condition to be treated. In general each dosage form will comprise from 1 mg to 100 mg of acid susceptible proton pump inhibitor and from 1 to 800 mg of the H2 receptor antagonist. Preferably each dosage form will comprise from 5 to 50 mg of the acid susceptible proton pump inhibitor and from 5 to 200 mg of the H2 receptor antagonist. The multiple unit tablet preparation is also suitable for dispersion in water which had been made slightly acidic by the addition of citric acid.

Example 1

Multiple unit tabletted dosage form comprising magnesium omeprazole and ranitidine hydrochloride; batch size 400 tablets. For omeprazole Mg-salt pellet production (core material, separating layer, enteric coating layer and over-coating layer, see WO 97/25066, p. 22-23 under respective headings), see WO 97/25066, first two paragraphs, all of which is hereby incorporated by reference.

| Tablets | |
|---|---|
| Prepared pellets comprising omeprazole Mg-salt | 31.3 g |
| Microcrystalline cellulose | 300.0 g |
| Cimetidine hydrochloride | 40.0 g |
| Potato starch | 50.0 g |
| Water | 200.0 g |
| PVP crosslinked | 38.0 g |
| Sodium stearyl fumarate | 4.6 g |

A small amount of the potato starch is dissolved in purified hot water to form the granulation liquid. Cimetidine hydrochloride, the rest of potato starch and microcrystalline cellulose are dry mixed. The granulation liquid is added to the dry mixture and the mass is wet mixed. The wet mass is dried in an oven at 50° C. The prepared granulation is milled through sieve 1 mm in an oscillating mill equipment. The enteric coating layered pellets with an over-coating layer, the prepared H2 receptor antagonist granules, crosslinked polyvinylpyrrolidone and sodium stearyl fumarate are mixed and compressed into tablets using a tabletting machine equipped with oval punches. The amount of omeprazole in each tablet is approx. 10 mg and the amount of cimetidine hydrochloride is approx. 100 mg.

By a slight modification this multiple unit tablet form can be made to comprise an antacid agent (instead of microcrystalline cellulose, 300 mg: microcrystalline cellulose, 100 g; calcium carbonate, 100 mg; magnesium oxide, 100 mg; all other constituents, except water, in the amounts given above).

Example 2

Three-layered tabletted dosage form. The tablet comprises the acid susceptible proton pump inhibitor omeprazole, a separating layer and a core layer comprising cimetidine hydrochloride. Batch size 1000 tablets.

| First tablet layer | |
|---|---|
| Cimetidine hydrochloride | 200.0 g |
| Microcrystalline cellulose | 250.0 g |
| PVP crosslinked | 13.0 g |
| Sodium stearyl fumarate | 3.8 g |
| Separating layer | |
| Microcrystalline cellulose | 80.0 g |
| Second tablet layer | |
| Enteric coating layered pellets comprising omeprazole magnesium salt (same as in EXAMPLE 1) | 78.3 g |
| Microcrystalline cellulose | 174.0 g |
| PVP crosslinked | 26.0 g |
| Sodium stearyl fumarate | 1.4 g |

The constituents of the first tablet layer are dry mixed and precompressed as a first layer in a tabletting machine equipped with oval punches. Microcrystalline cellulose is filled on the top of the first layer to form a separating layer to the next layer. The constituents of the second tablet layer are dry mixed and filled on top of the separating layer. The three layers are compressed into a three layer tablet which may be coated by a tablet coating layer. The amount of omeprazole is approx. 10 mg and that of cimetidine hydrochloride approx. 200 mg per tablet.

Example 3

Capsule dosage form. No. 1 hard gelatin capsules (16) (FIG. 5; volume 0.48 ml) were filled with enteric coated omeprazole pellets (15) containing 20 mg omeprazole recovered from commercially available omeprazole (Losec®) capsules and a dry mixture 14 of commercially available famotidine 20 mg for injection (Pepcidin®; containing 20 mg famotidine hydrochloride, 8 mg aspartic acid and 40 mg mannitol), and closed.

Example 4

Divided powder/pellet formulation. Enteric pellets containing 15 mg lansoprazole recovered from commercially available capsules (Lanzo®, enterocapsules) and the famotidine preparation for injection of EXAMPLE 4 were dry mixed with citric acid. Single dose portions thereof containing 10 mg each of lansoprazole and famotidine hydrochloride and 200 mg powderous citric acid were dry packed in plastic laminate. The composition is intended to be poured into 20 ml of water, stirred for a short time, and swallowed.

Example 5

Multiple unit capsule dosage form. The tabled comprises magnesium omeprazole and famotidine hydrochloride. For enteric coating layer and over-coating layer, see WO 97/25066, page 22-23 under respective headings, the information under which is hereby incorporated by reference.

Magnesium omeprazole is mixed with microcrystalline cellulose spheres to an ordered mixture. The ordered mixture is coated with an enteric coating layer consisting of methacrylic acid copolymer, mono- and diglycerides, triethyl citrate and polysorbate in a fluid bed apparatus. The enteric coated ordered mixture is then over-coated with a water suspension containing famotidine hydrochloride, hydroxypropylmethyl cellulose and magnesium stearate in a fluid bed apparatus. The enteric coated ordered mixture with an over-coating layer was filled in hard gelatin capsules. The amount of omeprazole is approx. 10 mg and that of famotidine hydrochloride approx. 20 mg per capsule.

Example 7

Multiple unit tabletted dosage form comprising magnesium omeprazole and cimetidine hydrochloride. Magnesium omeprazole is mixed with microcrystalline cellulose spheres to an ordered mixture which is coated with an enteric coating layer as described in EXAMPLE 6. Cimetidine hydrochloride is granulated as described in EXAMPLE 1. The enteric coated ordered mixture comprising magnesium omeprazole, the cimetidine granules and excipients are dry mixed and compressed into tablets. The amount of omeprazole in each tablet is approx. 10 mg and that of cimetidine is approx. 100 mg.

Example 8

Figure 7:
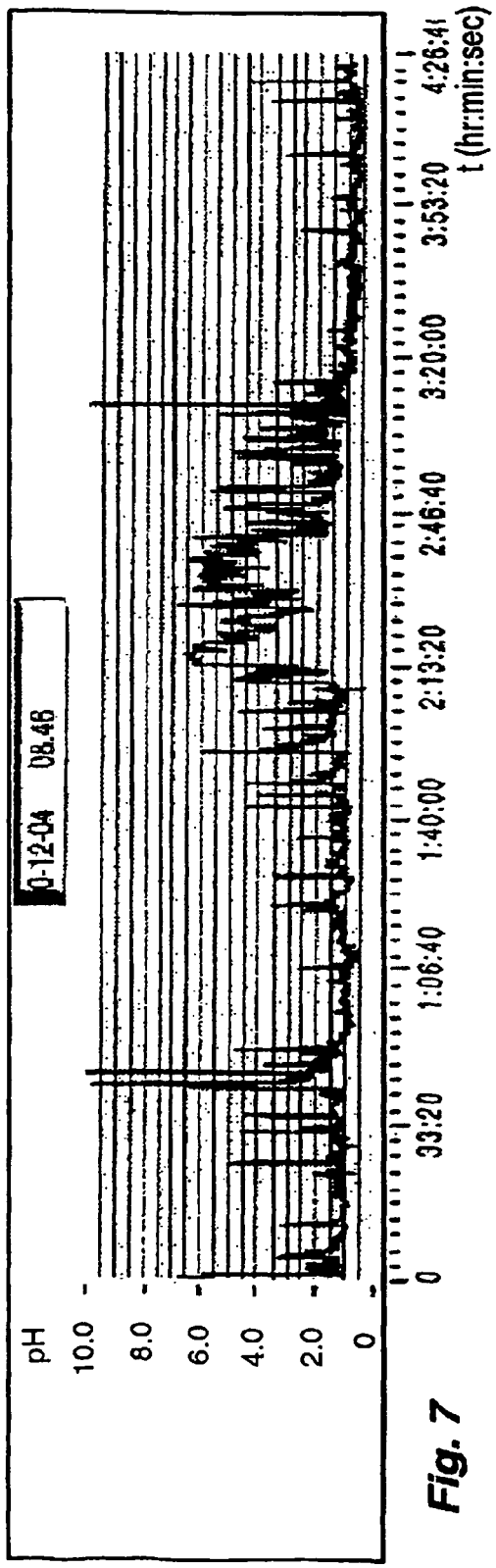
FIG. 7 is a diagram of the gastric pH trace in a person after administration of a conventional omeprazole oral dosage form.
Figure 8:
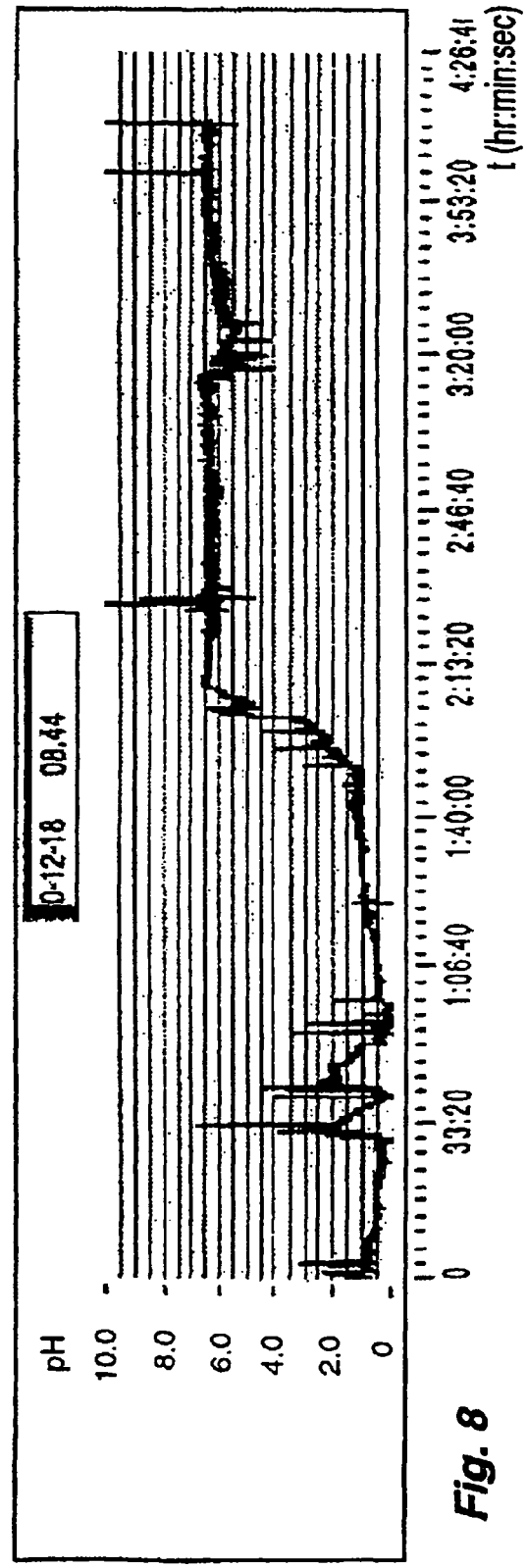
FIG. 8 is a diagram of the gastric pH trace in the same person after joint administration of omeprazole and famotidine according to the invention.

Inhibition of gastric acid secretion. A healthy subject (male, 31 years of age, having fasted for 10 hours) was provided with a double lumen nasogastric tube through one nasal passage and with a microelectrode for pH registration through the second nasal passage. A two point calibration of the electrode was performed before and after each 24 h recording, using standard buffers of pH 7.0 and 1.7. The electrode was placed 10 cm below the lower esophagal sphincter during the pH recording and the position marked on the electrode lead to ensure proper positioning during consecutive recordings. A commercially available omeprazole (Losec®) capsule containing 20 mg omeprazole was carefully opened and the contents (pellets) placed in a plastic syringe which had been put into communication with one of the lumina of the nasogastric tube. The syringe was filled with 20 ml tap water and the pellets injected through the nasogastric tube immediately thereafter. The syringe was flushed with 20 ml water. The gastric pH trace recorded by the microelectrode during a period of more than four hours is illustrated in FIG. 7. In a second experiment the syringe was filled with the same amount of omeprazole micropellets and famotidine 20 mg for injection (Pepcidin®; containing 20 mg famotidine, 8 mg aspartic acid and 40 mg mannitol), the procedure of injection and measurement being the same as with omeprazole. The gastric pH trace for the combination is illustrated in FIG. 8. The experiments demonstrate that a reduction of pH to about 6 is obtained with the omeprazole/famotidine within about 2 hours and maintained until the end of recording (4 hours from injection) whereas with omeprazole alone no increase in pH can be noted after 4 hours from injection.

The invention claimed is:

1. A method for the treatment of at least one symptom of gastro-esophageal reflux disease (GERD) in a human suffering from GERD consisting essentially of administering an oral pharmaceutical dosage form into a gastro-intestinal tract of a human suffering from GERD, the oral pharmaceutical dosage form consisting essentially of a proton pump inhibitor or a salt thereof (PPI), an H2 receptor antagonist or a salt thereof (H2RA), a pharmaceutically acceptable carrier, an enteric coating on the PPI that separates the PPI from the H2RA, and optionally an antacid agent and/or alginate, wherein the PPI is selected from lansoprazole, omeprazole, pantoprazole, rabeprazole, pariprazole, leminoprazole, their pharmaceutically acceptable salts, enantiomers and salts of enantiomers, wherein the H2RA is selected from cimetidine, ranitidine, nizatidine and famotidine, their pharmaceutically acceptable salts, isomers and salts of isomers, and wherein administering the oral pharmaceutical dosage form orally introduces into the gastro-intestinal tract of the human suffering from GERD the PPI in combination with the H2RA separated from the PPI by the enteric coating.

2. A method as claimed in claim 1, wherein the oral pharmaceutical dosage form is administered to affect a rise in gastric pH above 3 within about 2 hours from the administration of the first dose, thereby treating the human suffering from GERD promptly, and wherein the administering is repeated, if necessary to treat the human suffering from GERD over a prolonged period until 6 hours from the administration of the last dose.

3. A method as claimed in claim 1, wherein the at least one symptom of gastro-esophageal reflux disease is indigestion, heartburn, sour stomach and/or upper abdominal pain and/or discomfort.

4. A method as claimed in claim 1, wherein the PPI is in the amount of from 1 mg to 100 mg and/or the H2RA is in the amount of from 1 mg to 800 mg in combination with the PPI.

5. A method as claimed in claim 1, wherein the optional antacid agent in the oral pharmaceutical dosage form is one or several of aluminum hydroxide, calcium carbonate, magnesium carbonate, basic magnesium carbonate, magnesium hydroxide, magnesium oxide and/or sodium hydrogen carbonate.

6. A method as claimed in claim 1, wherein the oral pharmaceutical dosage form is in the form of two concentric layers optionally separated by one or more separating layer(s), wherein the inner concentric layer is the PPI and the outer concentric layer is the H2RA.

7. A method as claimed in claim 1, wherein the oral pharmaceutical dosage form is in the form of a capsule, a divided powder/pellet formulation or a tablet.

8. A method as claimed in claim 1, wherein the oral pharmaceutical dosage form is the PPI in the form of individual enterically coated layered units and the H2RA in the form of a powder or granules compressed into a tablet.

9. A method as claimed in claim 1, wherein the oral pharmaceutical dosage form is a capsule dosage form containing the PPI in the form of enterically-coated layered pellets in admixture with the H2RA and a pharmaceutical excipient.

10. A method as claimed in claim 1, wherein the oral pharmaceutical dosage form is in the form of the PPI enterically coated to separate the PPI from the H2RA.

11. A method as claimed in claim 10, wherein the PPI is in the form of a core and the H2RA is in the form of a layer surrounding the core, and wherein the enteric coating separates the core from the layer surrounding the core.

12. A method as claimed in claim 1, wherein the oral pharmaceutical dosage form is in the form of a core of the PPI free of the H2RA and a layer surrounding the core which separates the core from the enteric coating.

* * * * *